United States Patent [19]

Kadokura et al.

[11] Patent Number: 4,650,895

[45] Date of Patent: Mar. 17, 1987

[54] PROCESS FOR PRODUCING HIGH PURITY METALLIC COMPOUND

[75] Inventors: Hidekimi Kadokura; Hiroshi Umezaki; Yoshihiro Higuchi, all of Niihama, Japan

[73] Assignee: Sumitomo Chemical Company, Limited, Osaka, Japan

[21] Appl. No.: 575,146

[22] Filed: Jan. 30, 1984

[30] Foreign Application Priority Data

Feb. 9, 1983 [JP] Japan .................................. 58-20986
Feb. 9, 1983 [JP] Japan .................................. 58-20987

[51] Int. Cl.[4] ............................................ C07F 5/06

[52] U.S. Cl. .................................. 556/182; 423/598; 423/608; 423/609; 423/610; 423/618; 423/629; 556/1; 556/54; 556/89; 556/482; 556/187

[58] Field of Search ........ 260/448 A, 448 AD, 429.5; 556/1, 54, 89, 482, 182; 423/598, 629, 608, 609, 610, 618

[56] References Cited

U.S. PATENT DOCUMENTS 2,727,918 12/1955 Boyd .......................... 260/429.5 X
2,768,907 10/1956 Lusby ......................... 260/429.5 X

OTHER PUBLICATIONS

Leiss, Organometallic Chemistry, Reinhold Publ. Corp., N.Y., Chapman & Hall, N.Y., pp. 236, 238 & 239 (1960).

Mole et al., Organoaluminum Compounds, Elsevier Publ. Co., N.Y., pp. 211–212 (1972).

Nesmeyanov et al., Methods of Elements-Organic Chemistry, North Holland Publ. Co., Amsterdam, vol. 1, pp. 363, 404, 423, 457 to 459 (1967).

Chemical Abstracts 53 14388i (1959).

Bradley et al., Metal Alkoxides, Academic Press, N.Y., pp. 150–167 (1978).

Feld et al., The Organic Chemistry of Titanium, Butterworths, Wash. D.C., pp. 25–31 (1965).

Chemical Reviews 61 15–17 (1961).

*Primary Examiner*—Helen M. S. Sneed

*Attorney, Agent, or Firm*—Stevens, Davis, Miller & Mosher

[57] ABSTRACT

High purity organometallic compounds can be obtained by the process which comprises subjecting an organometallic compound in a liquid state under stirring to preliminary oxidation or hydrolysis in a proportion of about 0.1 to 50% by weight of the organometallic compound to form solid reaction products, and separating by distillation the unreacted organometallic compound from the solid reaction products to recover the purified organometallic compound; and high purity metallic compounds such as a solid metallic hydroxide or oxide can be obtained by the process which comprises following the process as mentioned above, oxidizing or hydrolyzing completely the recovered purified organometallic compound.

7 Claims, No Drawings

PROCESS FOR PRODUCING HIGH PURITY METALLIC COMPOUND

This invention relates to processes for producing metallic compounds, and more particularly to a process for producing organometallic compounds freed from impurity elements originally present in minute amounts in the compounds and to a process for producing high purity metal hydroxides or oxides from said organometallic compounds.

Hereinafter this invention is described referring to organoaluminum compounds as representatives of said organometallic compounds and to aluminum oxide as a representative of said metal hydroxides or oxides. However, it is obvious that the processes of this invention are not-limited to these aluminum compounds.

Organoaluminum compounds are useful as polymerization catalysts and raw materials for producing olefins, higher alcohols, and high purity alumina.

However, usual organoaluminum compounds contain minute amounts of some of the elements and metallic compounds including titanium, vanadium, chromium, manganese, iron, cobalt, nickel, copper, uranium, silicon, etc. and their compounds (hereinafter these elements and metal compounds are referred to as impurities). These impurities in organoaluminum compounds come from raw material aluminum for synthesizing the organoaluminum compounds, reactor materials through extraction, or additives or the like used for promoting reactions in the synthesis of the organoaluminum compounds.

The presence of impurities in organoaluminum compounds results in various disadvantages in the above-mentioned applications. The disadvantages, for example, are as follows: When olefins are produced by the oligomerization of ethylene in the presence of a catalytic amount of an alkylaluminum compound, an undesirable polymer yields as a by-product; When propagation reaction is conducted by addition of ethylene to an alkylaluminum compound, release of olefin occurs to hinder the propagation; When an alumina is produced by the hydrolysis of an alkylaluminum compound, high purity aluminum hydroxide or alumina cannot be produced.

Rectification or the like readily comes into one's mind as a method for removing said impurities from organoaluminum compounds. In this case, however, it is essentially difficult to recover by rectification the product with a required purity of at least 99.9%. This is because some impurities present in organoaluminum compounds are organometallic compounds having the same organic groups as of the organoaluminum compounds and hence have boiling points ranging close to those of the organoaluminum compounds. This method has also the disadvantages of requiring a complicated and expensive facility.

Under such circumstances, the present inventors made intensive studies for the purpose of finding out an industrial process for highly effective removal of impurities present in minute amounts in organometallic compounds. As a result, this invention has been accomplished through finding such unexpected behavior of the above impurities in organometallic compounds that these impurities are concentrated in the reaction products when the impurity-containing organometallic compounds are subjected to preliminary oxidation or hydrolysis (hereinafter referred to as the preliminary reaction) under specific conditions and then to distillation.

One object of this invention is to provide a novel process for obtaining organometallic compounds substantially or completely free of impurities.

Another object of this invention is to provide a novel process for obtaining metal hydroxides or oxides substantially or completely free of impurities.

These and other objects and advantages of this invention will be apparent to persons skilled in the art from the following description.

Thus, the invention provides a process for producing high purity organometallic compounds which comprises subjecting an organometallic compound in a liquid state under stirring to oxidation or hydrolysis with a reactant preliminarily in a proportion of about 0.1 to about 50% by weight of the organometallic compound form solid reaction products, and separating by distillation the unreacted organometallic compound from the solid reaction products to recover the purified organometallic compound.

This invention also provides a process for producing high purity metal hydroxides or oxides which comprises subjecting an organometallic compound in a liquid state under stirring to oxidation or hydrolysis with a reactant preliminarily in a proportion of about 0.1 to about 50% by weight of the compound to form solid reaction products, separating by distillation the unreacted organometallic compound from the solid reaction products to recover the purified organometallic compound, and hydrolyzing or oxidizing completely the recovered organometallic compound.

The starting organometallic compound used in the production of high purity organometallic compounds, metal hydroxides, or metal oxides according to the process of this invention contains at least one impurity constituted of a metal other than the constituent metal of the mother liquor organometallic compound. Such an impurity is a metal or metal compound other than the constituent metal of the mother liquor or the compounds of this constituent metal. Examples of the impurity-constituting metal are titanium, vanadium, chromium, manganese, iron, cobalt, nickel, copper, aluminum, gallium, uranium, and the like.

The concentration of impurities in the organometallic compound to be purified according to the process of this invention, though not particularly restricted, is generally about 0.01 to about 0.5% by weight.

Organometallic compounds used as starting materials in this invention include those represented by the general formula

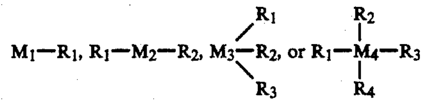

wherein; $M_1$, $M_2$, $M_3$, and $M_4$ denote monovalent, divalent, trivalent, and tetravalent elements, respectively; and $R_1$, $R_2$, $R_3$, and $R_4$ are the same or different and denote each an alkyl, aryl, alkoxy, or aryloxy group or a halogen or hydrogen atom.

For example; $M_1$ is Li; $M_2$ is Mg, Ca, Ba, Co, Mn, Zn or Cd; $M_3$ is B, Al, Ga, In, Y, La, Cr, Fe, Mo, or W; and $M_4$ is Si, Ti, Ge, Zr, Sn, Hf, Ni, Cu, Th, or U. Organometallic compounds having such $M_1$, $M_2$, $M_3$, or $M_4$ are the objects of the treatment.

Preferred objects of the treatment are organometallic compounds of Al, Ga, In, Si, Ti, Zr or Sn having a $C_1$–$C_{12}$ alkyl or $C_1$–$C_8$ alkoxy group.

Particularly preferred objects of the treatment are organoaluminum compounds such as triethylaluminum, tripropylaluminum, tributylaluminum, trihexylaluminum, dibutylaluminum hydride, dihexylaluminum hydride, dioctylaluminum hydride, triethoxyaluminum, tripropoxyaluminum, tributoxyaluminum, and triamyloxyaluminum.

The above impurity-containing organometallic compound can be subjected alone or in mixture with an organic solvent to the purification treatment (preliminary reaction) according to the process of this invention.

Organic solvents usable for preparing the mixture include; saturated aliphatic hydrocarbons such as pentane, hexane, octane, decane, dodecane, paraffin oil, and kerosene; unsaturated aliphatic hydrocarbons such as pentene, hexene, heptene, octene, decene, and dodecene; alicylic hydrocarbons such as cyclohexane and cyclopentane; aromatic hydrocarbons such as benzene and toluene; alcohols such as methanol, ethanol, propanol, and butanol; and ethers such as diethyl ether, dipropyl ether, anisole, dioxane, and tetrahydrofuran.

In the preliminary reaction process of this invention, the above impurity-containing organometallic compound is subjected to oxidation or hydrolysis in a proportion of about 0.1 to about 50% by weight thereof under stirring while keeping it in a liquid state.

It is essential to carry out the preliminary reaction under stirring while keeping the organometallic compound in a liquid state. Proper conditions of the stirring can be readily determined by trial experiments. Usually suitable stirring speeds in the reaction are 10 to 200 rpm.

When the preliminary reaction is carried out under stirring while keeping the organometallic compound in a liquid state, the reaction of coexisting impurities takes place together with the reaction of the organometallic compound. In this case, conceivably the reaction of impurities proceeds preferentially, so that the impurities remove substantially or completely from the unreacted organometallic compound phase to the solid reaction product phase after the preliminary reaction has been conducted to the prescribed extent.

If the preliminary reaction is conducted without stirring, the impurities cannot substantially be removed even though the organometallic compound is kept in a liquid state, since the reaction occurs locally.

Reactants generally used are water, water vapor, acidic aqueous solution, oxygen, and air. Preferably, the reactant is fed to the reactor after being diluted with an organic solvent in the case of water or acidic aqueous solution, and with an inert gas such as argon, nitrogen, or the like in the case of oxygen or air, though these reactant of course can be fed as such without dilution.

For the purification treatment of the organometallic compound (preliminary reaction) according to this invention, the reactant is used in such amounts so as to oxidize or hydrolyze generally about 0.1 to about 50%, preferably about 1 to about 20%, of the starting impurity-containing organometallic compound. The proportion of the reacted organometallic compound, if less than 0.1%, results in undesirably low percentages of impurity removal, and if exceeding 50%, results in worse economy though the percentage of impurity removal becomes better.

The reaction is favorably carried out at a temperature of about 0° to about 150° C., preferably 20° to 120° C. Any method is applicable for contacting the organometallic compound with the reactant. In general, a suitable method for the contact is to add the reactant to the organometallic compound while stirring it.

However, other stirring methods such as the mixing by gas blowing are possible, and for adding the reactant, the method of feeding it into the liquid and some other methods are applicable.

After the preliminary reaction, the organometallic compound is subjected to distillation as it is or after being separated from the solid reaction products by sedimentation on standing, filtration, or centrifugation.

The organometallic compound thus purified preliminarily is further subjected to a distillation such as simple distillation, fractional distillation, or vacuum distillation. A suitable distillation method may be optionally employed depending upon the desired purity of the product organometallic compound. The distillation temperature may be chosen depending upon properties (boiling point, thermal stability, etc.) of the organometallic compound to be distilled.

Generally, the distillation is desired to be carried out at a reduced pressure of 0.1 to 100 mmHg and in the temperature range of 50° to 250° C.

Distillation is an essential operation in the purification process of this invention. Without distillation, it is impossible to remove the impurities effectively.

The above process of this invention is effective for removing impurities from organometallic compounds containing several percentage or less, particularly 1 to 1000 ppm, of impurities and is suited for producing organometallic compounds of extremely high purity, e.g. at least 99.9%.

In the process of this invention for producing high purity metal hydroxides or oxides, organometallic compounds purified as described above are then subjected to complete oxidation or hydrolysis (hereinafter referred to as the main reaction).

The main reaction is accomplished by contacting a reactant with the purified organometallic compound while keeping it in a liquid state, with or without stirring, but preferably with stirring.

Reactants generally usable are water, water vapor, acidic aqueous solution, oxygen, and air. Preferably, the reactant is fed to the reactor after dilution with an organic solvent in the case of water or acidic aqueous solution and with an innert gas such as argon, nitrogen, or the like in the case of oxygen or air, though these reactants can be fed as such without dilution.

While the amount of the reactant used is optional, nearly stoichiometric amounts or more of the reactant may be used in general.

The main reaction is generally carried out in the temperature range of about 0° to about 150° C.

For the main reaction, the purified organometallic compound can be supplied alone or in mixture with an organic solvent.

Such organic solvents include; saturated aliphatic hydrocarbons such as pentane, hexane, octane, decane, dodecane, paraffin oil, and kerosene; unsaturated hydrocarbons such as pentene, hexene, heptene, octene, decene, and dodecene; alicyclic hydrocarbons such as cyclohexane and cyclopentane; aromatic hydrocarbons such as benzene and toluene; alcohols such as methanol, ethanol, propanol, and butanol; and ethers such as diethyl ether, dipropyl ether, anisole, dioxane, and tetrahydrofuran.

From the product mixture of the main reaction carried out as described above, the metal hydroxide or oxide is isolated by a known method such as filtration, sedimentation, centrifugation, or distillation.

The thus obtained metal hydroxide or oxide has an extremely high purity, i.e. a purity of at least 99.9%.

According to the first process of this invention mentioned in detail above, impurities can be removed substantially or completely from organometallic compounds. The thus purified organometallic compounds can be effectively utilized as polymerization catalysts and starting materials for producing olefins, higher alcohols, and high purity metal oxides, without giving rise to any of such disadvantages as stated referring to the prior art. This indicates great industrial value of the invention.

Additionally, according to the second process of this invention mentioned in detail above, impurities can be removed substantially or completely from organometallic compounds and high purity metal hydroxides or oxides can be produced from the thus purified organometallic compounds. This also indicates great industrial value of the invention.

The invention is illustrated in more detail with reference to the following examples; however, the invention is not limited to these examples but can be modified within the spirit and scope of the invention.

EXAMPLE 1

In a 5-l reactor equipped with a stirrer, condenser, and water-dropping funnel, was charged 570 g of triethylaluminum containing various impurities in concentrations as shown in Table 1, and 18 g of water diluted with 1000 ml of tetrahydrofuran was added over 1 hour with stirring at 100 rpm while keeping the temperature at 65° C., to hydrolyze the triethylaluminum in part. The resulting solid reaction products were removed by filtration, the tetrahydrofuran was then eliminated from the filtrate by heating at 70° C., and 490 g of purified triethylaluminum was obtained by vacuum distillation at 10 mmHg and 97° C. The concentrations of various impurity elements in the purified triethylaluminum were as shown in Table 1.

TABLE 1

| | Concentrations of impurity elements (ppm) | |
|---|---|---|
| Element | Starting organometallic compound | Purified organometallic compound |
| Ti | 40 | <1 |
| Fe | 480 | 1 |
| Cu | 80 | <1 |
| Si | 620 | 1 |
| Na | 20 | <1 |
| U | 2 | <0.001 |

EXAMPLE 2

In the same reactor as used in Example 1, were charged 992 g of triisobutylaluminum containing various impurities in concentrations as shown in Table 2, and 1000 ml of tetrahydrofuran. Then, 1.8 g of water diluted with 100 ml of tetrahydrofuran was added over 1 hour with stirring at 100 rpm while keeping the temperature at 65° C., to hydrolyze the triisobutylaluminum in part. The resulting solid reaction products were removed by filtration, the tetrahydrofuran was then eliminated from the filtrate by heating at 70° C., and 850 g of purified triisobutylaluminum was obtained by vacuum distillation at 10 mmHg and 85° C. The concentrations of various impurity elements in the purified triisobutylaluminum were as shown in Table 2.

TABLE 2

| | Concentrations of impurity elements (ppm) | |
|---|---|---|
| Element | Starting organometallic compound | Purified organometallic compound |
| Ti | 210 | 1 |
| Fe | 460 | 1 |
| Cu | 80 | <1 |
| Si | 690 | 2 |
| Na | 20 | <1 |
| U | 2 | <0.001 |

EXAMPLE 3

Aluminum isopropoxide was purified by way of partial hydrolysis with three different amounts of water. Each of the purification experiments was conducted as follows: In the same reactor as used in Example 1, were charged 1020 g of aluminum isopropoxide containing impurities in concentrations as shown in Table 3 and 1500 ml of isopropanol. An amount shown in Table 3 of water diluted with 200 ml of isopropanol was added over 1 hour with stirring at 100 rpm while keeping the temperature at 80° C., to hydrolyze the aluminum isopropoxide in part. The resulting solid reaction products were removed by filtration, the isopropanol was then eliminated from the filtrate by heating at 90° C., and about 940 g of purified aluminum isopropoxide was obtained by vacuum distillation at 10 mmHg and 135° C. The concentrations of impurity elements in the aluminum isopropoxide products thus obtained using different amounts of water were as shown in Table 3.

TABLE 3

| Run No. | | | 1 | 2 | 3 (Control) |
|---|---|---|---|---|---|
| | | Starting organometallic compound | Purified organometallic compound | | |
| Amount of water added (g) | | | 9 | 1.8 | 0.12 |
| Percentage of hydrolysis (%) | | | 5 | 1 | 0.07 |
| Concentration of impurity element (ppm) | Ti | 50 | <1 | 1 | 10 |
| | Fe | 750 | <1 | 1 | 60 |
| | Cu | 80 | <1 | <1 | 10 |
| | Si | 200 | <1 | 3 | 60 |
| | Na | 40 | <1 | <1 | 5 |
| | U | 2 | <0.001 | <0.001 | 0.1 |

From the above results it has proved that impurities in the starting material organometallic compound can be removed effectively by hydrolyzing at least about 0.1% of the starting material.

EXAMPLE 4

In the same reactor as used in Example 1, were charged 1422 g of titanium isopropoxide containing impurities in concentrations as shown in Table 4 and 1500 ml of isopropanol. Then, 9 g of water diluted with 200 ml of isopropanol was added over 1 hour with stirring at 100 rpm while keeping the temperature at 80°

C., to hydrolyze the titanium isopropoxide in part. The resulting solid reaction products were removed by filtration, the isopropanol was then eliminated from the filtrate by heating at 90° C., and 1280 g of purified titanium isopropoxide was obtained by vacuum distillation at 10 mmHg and 116° C. The concentration of various impurity elements in the purified titanium isopropoxide thus obtained were as shown in Table 4.

TABLE 4

| Element | Concentrations of impurity elements (ppm) | |
|---|---|---|
| | Starting organometallic compound | Purified organometallic compound |
| Fe | 880 | 2 |
| Si | 370 | 1 |
| Na | 480 | 3 |
| V | 110 | 2 |
| U | 1 | <0.001 |

EXAMPLE 5

(The preliminary reaction)

In a 5-l reactor equipped with a stirrer, condenser, and water-dropping funnel, was charged 570 g of triethylaluminum containing various impurities in concentrations as shown in Table 5. Then, 18 g of water diluted with 1000 ml of tetrahydrofuran was added over 1 hour with stirring at 100 rpm while keeping the temperature at 65° C., to hydrolyze the triethylaluminum preliminarily. The resulting solid reaction products were removed by filtration, the tetrahydrofuran was then eliminated from the filtrate by heating at 70° C., and 490 g of purified triethylaluminum was obtained by vacuum distillation at 10 mmHg and 97° C.

(The main reaction)

In a 5-l reactor equipped with a stirrer, condenser, and water-dropping funnel, were charged 490 g of the purified triethylaluminum obtained above and 500 ml of tetrahydrofuran. Then, 300 g of water diluted with 1000 ml of tetrahydrofuran was added over 3 hours with stirring at 100 rpm while keeping the temperature at 65° C., to hydrolyze the triethylaluminum completely, giving aluminum hydroxide.

The concentrations of various impurity elements in the thus obtained aluminum hydroxide were as shown in Table 5.

TABLE 5

| Element | Concentrations of impurity elements (ppm) | |
|---|---|---|
| | Starting organometallic compound | Product aluminum hydroxide |
| Ti | 40 | <1 |
| Fe | 480 | 1 |
| Cu | 80 | <1 |
| Si | 620 | 1 |
| Na | 20 | <1 |
| U | 2 | <0.001 |

EXAMPLE 6

(The preliminary reaction)

In the same reactor as used in Example 5 were charged 992 g of triisobutylaluminum containing various impurities in the concentrations as shown in Table 6, and 1000 ml of tetrahydrofuran. Then, 1.8 g of water diluted with 100 ml of tetrahydrofuran was added over 1 hour with stirring at 100 rpm while keeping the temperature at 65° C., to hydrolyze the triisobutylaluminum preliminarily. The resulting solid reaction products were removed by filtration, the tetrahydrofuran was then eliminated from the filtrate by heating at 70° C., and 850 g of purified triisobutylaluminum was obtained by vacuum distillation at 10 mmHg and 85° C.

(The main reaction)

In the same reactor as used in Example 5, were charged 850 g of the purified trilisobutylaluminum obtained above and 500 ml of tetrahydrofuran. Then, the trilisobutylaluminum was completely hydrolyzed with stirring at 100 rpm while keeping the temperature at 65° C. The concentrations of various impurity elements in the thus obtained aluminum hydroxide were as shown in Table 6.

TABLE 6

| Element | Concentrations of impurity elements (ppm) | |
|---|---|---|
| | Starting organometallic compound | Product aluminum hydroxide |
| Ti | 210 | 1 |
| Fe | 460 | 1 |
| Cu | 80 | <1 |
| Si | 690 | 2 |
| Na | 20 | <1 |
| U | 2 | <0.001 |

EXAMPLE 7

Aluminum isopropoxide was purified by way of preliminary hydrolysis with three different amounts of water and aluminum hydroxide was prepared by complete hydrolysis of the purified aluminum isopropoxide. Each of the experiments was conducted as follows:

(The preliminary reaction)

In the same reactor as used in Example 5, were charged 1020 g of aluminum isopropoxide containing impurities in concentrations as shown in Table 7 and 1500 ml of isopropanol. An amount shown in Table 7 of water diluted with 200 ml of isopropanol was added over 1 hour with stirring at 100 rpm while keeping the temperature at 80° C., to hydrolyze the aluminum isopropoxide preliminarily. The resulting solid reaction products were removed by filtration, the isopropanol was then eliminated from the filtrate by heating at 90° C., and about 940 g of purified aluminum isopropoxide was obtained by vacuum distillation at 10 mmHg and 135° C.

(The main reaction)

In the same reactor as used in Example 5, were charged 940 g of the purified aluminum isopropoxide obtained above and 1500 ml of isopropanol. Then, 300 g of water diluted with 500 ml of isopropanol was added over 3 hours with stirring at 100 rpm while keeping the temperature at 80° C., to hydrolyze the aluminum isopropoxide completely giving aluminum hydroxide.

The concentrations of various impurity elements in the aluminum hydroxide products prepared in this way were as shown in Table 7.

TABLE 7

| Run No. | | 1 | 2 | 3 (Control) |
|---|---|---|---|---|
| | Starting organometallic compound | Purified organometallic compound | | |
| Amount of water added | | 9 | 1.8 | 0.12 |

TABLE 7-continued

| Run No. | | | 1 | 2 | 3 (Control) |
|---|---|---|---|---|---|
| (g) | | | | | |
| Percentage of hydrolysis (%) | | | 5 | 1 | 0.07 |
| Concentration of impurity element (ppm) | Ti | 50 | <1 | 1 | 10 |
| | Fe | 750 | <1 | 1 | 60 |
| | Cu | 80 | <1 | <1 | 10 |
| | Si | 200 | <1 | 3 | 60 |
| | Na | 40 | <1 | <1 | 5 |
| | U | 2 | <0.001 | <0.001 | 0.1 |

From the above results, it has proved that impurities in the starting material organometallic compound can be removed effectively by hydrolyzing at least about 0.1% of the starting material.

EXAMPLE 8

(The preliminary reaction)

In the same reactor as used in Example 5, were charged 1422 g of titanium isopropoxide containing impurities in concentrations as shown in Table 8 and 1500 ml of isopropanol. Then, 9 g of water diluted with 200 ml of isopropanol was added over 1 hour with stirring at 100 rpm while keeping the temperature at 80° C., to hydrolyze the titanium isopropoxide preliminarily. The resulting solid reaction products were removed by filtration, the isopropanol was then eliminated from the filtrate by heating at 90° C., and 1280 g of purified titanium isopropoxide was obtained by vacuum distillation at 10 mmHg and 116° C.

(The main reaction)

In the same reactor as used in Example 5, were charged 1280 g of the purified titanium isopropoxide obtained above and 1500 ml of isopropanol. Then, 300 g of water diluted with 500 ml of isopropanol was added over 3 hours with stirring at 100 rpm while keeping the temperature at 80° C., to hydrolyze the titanium isopropoxide completely, giving titanium hydroxide. The concentrations of various impurity elements in the thus prepared titanium hydroxide were as shown in Table 8.

TABLE 8

| | Concentrations of impurity elements (ppm) | |
|---|---|---|
| Element | Starting organometallic compound | Product titanium hydroxide |
| Fe | 880 | 2 |
| Si | 370 | 1 |
| Na | 480 | 3 |
| V | 110 | 2 |
| U | 1 | <0.001 |

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A process for producing high purity organometallic compounds which comprises subjecting an organometallic compound selected from the group consisting of Al, Ga, In, Si, Ti, Zr, and Sn compounds having a $C_1$–$C_{12}$ alkyl or a $C_1$–$C_8$ alkoxy group, in a liquid state under stirring to hydrolysis with a reactant preliminarily in a proportion of 0.1 to 50% by weight of the organometallic compound to form solid reaction products and then separating by distillation the unreacted organometallic compound from the solid reaction products to recover the purified organometallic compound.

2. A process according to claim 1, wherein the hydrolysis of the organometallic compound is conducted in a proportion of 1 to 20% by weight.

3. A process according to claim 1, wherein the hydrolysis is conducted at a temperature of 0° to 150° C.

4. A process according to claim 1, wherein the organometallic compound is an organoaluminum compound.

5. A process according to claim 1, wherein the reactant is water, water-vapor or acidic aqueous solution.

6. A process according to claim 1, wherein the hydrolysis is conducted in the presence of an organic solvent.

7. A process for producing high purity organometallic compounds which comprises subjecting an organometallic compound selected from the group consisting of Al, Ga, In, Si, Ti, Zr, and Sn compounds having a $C_1$–$C_{12}$ alkyl or a $C_1$–$C_8$ alkoxy group, in a liquid state under stirring to hydrolysis with a reactant preliminarily in a proportion of 0.1 to 50% by weight of the organometallic compound to form solid reaction products, separating by distillation the unreacted organometallic compound from the solid reaction products to recover the purified organometallic compound and then hydrolyzing completely the recovered organometallic compound to form a solid metal hydroxide or oxide.

* * * * *